United States Patent [19]

Svendsen

[11] Patent Number: 5,365,329
[45] Date of Patent: Nov. 15, 1994

[54] APPARATUS AND METHOD FOR MEASURING REFRACTIVE INDEX

[75] Inventor: David A. Svendsen, Winchester, United Kingdom

[73] Assignee: York Technology Limited, United Kingdom

[21] Appl. No.: 31,027

[22] Filed: Mar. 12, 1993

Related U.S. Application Data

[63] Continuation of Ser. No. 689,812, May 14, 1991, abandoned.

[30] Foreign Application Priority Data

Nov. 15, 1988 [GB] United Kingdom ............... 8826643

[51] Int. Cl.⁵ ............................................. G01N 21/45
[52] U.S. Cl. ................................. 356/73.1; 356/128
[58] Field of Search ............................. 356/73.1, 128

[56] References Cited

U.S. PATENT DOCUMENTS

| | | | |
|---|---|---|---|
| 4,181,433 | 1/1980 | Marcuse | 356/73.1 |
| 4,441,811 | 4/1984 | Melezoglu et al. | 356/128 |

FOREIGN PATENT DOCUMENTS

| | | |
|---|---|---|
| 96829 | 12/1983 | European Pat. Off. |
| 174708 | 3/1986 | European Pat. Off. |
| 63-95336 | 4/1988 | Japan ............... 356/73.1 |
| 2071315 | 9/1981 | United Kingdom |
| 2116708 | 9/1983 | United Kingdom |

OTHER PUBLICATIONS

Sasaki et al., "Measurement of Refractive-Index Profiles in Optical-Fiber Preforms by Spatial-Filtering Techniques" Electronics Letters, 13 Mar. 1980, vol. 16 #6, pp. 219–221.

Watkins "Laser beam refraction traversely through a grated-index preform to determine refractive index ratio and gradient profile" Applied Optics vol. 18, #13, 1 Jul. 1979 pp. 2214–2222.

Primary Examiner—Vincent P. McGraw
Attorney, Agent, or Firm—Dressler, Goldsmith, Shore & Milnamow, Ltd.

[57] ABSTRACT

A method of sensing optically properties of an approximately cylindrical object, such as an optical fibre or optical fibre preform, which diffracts the illuminating beam into a plurality of beam portions each corresponding to its respective diffraction order, comprising the steps of illuminating the object with an illuminating beam substantially perpendicular to the axis of the object, moving an aperture so as to discriminate a beam portion exiting from the object and corresponding to a selected diffraction order, and detecting said beam portion.

29 Claims, 7 Drawing Sheets

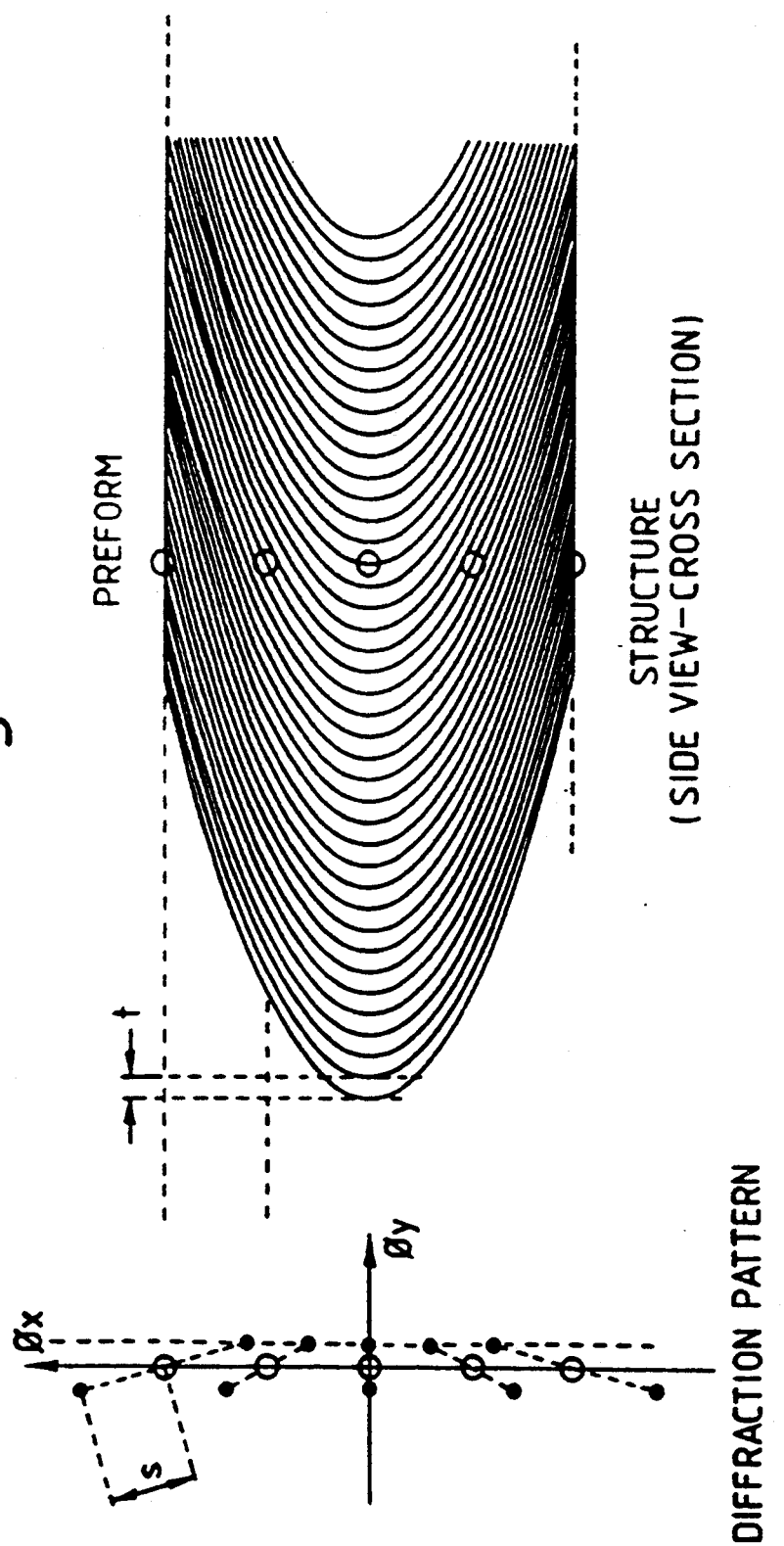

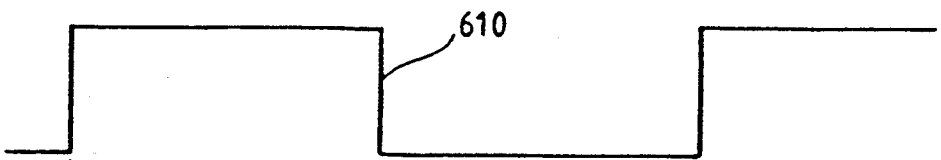
Fig.11a.
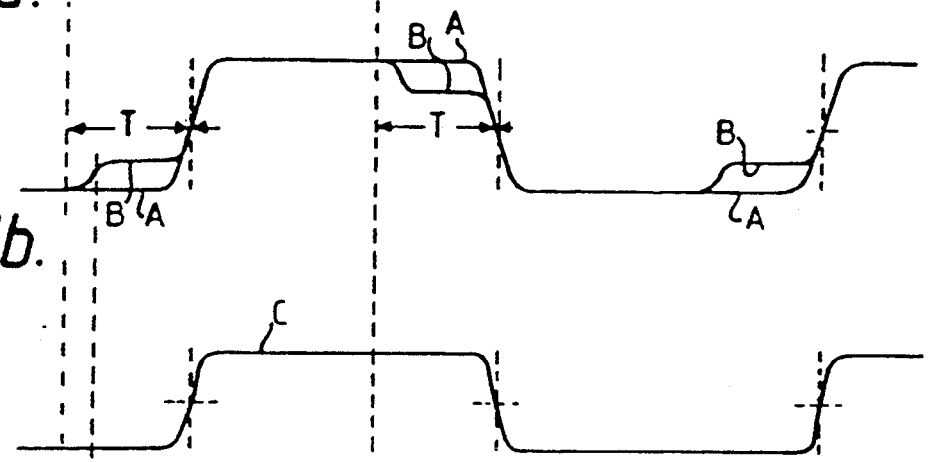
Fig.11b.
Fig.11c.
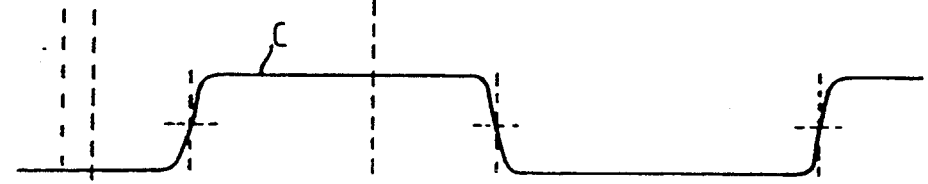
Fig.11d.
Fig.11e.
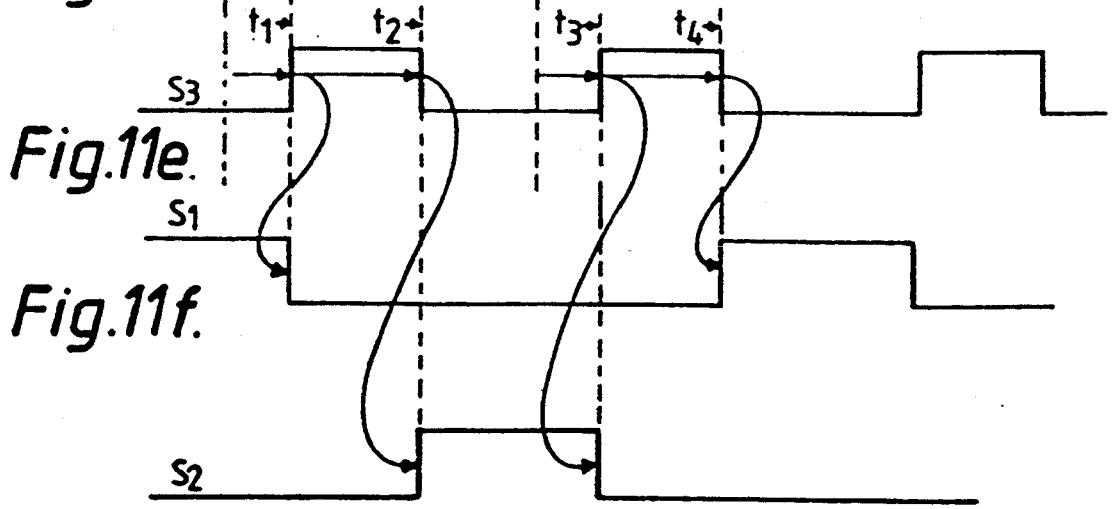
Fig.11f.
Fig.11g.

APPARATUS AND METHOD FOR MEASURING REFRACTIVE INDEX

This application is a continuation of application Ser. No. 07/689,812, filed May 14, 1991, now abandoned.

This invention relates to apparatus and a method for measuring by optical means the radial refractive index profile and other properties of a transparent object which is approximately cylindrical, such as an optical fibre or optical fibre preform, the measurement being made by illumination of the object generally transverse to the longitudinal axis of that object. The invention enables in particular the measurement of the radial refractive index profile of certain optical fibre preforms, such as those manufactured by the Vapour Axial Deposition (or VAD) process, which are not amenable to analysis by conventional apparatus and methods.

The refractive index profile of an optical fibre preform is usually required to consist of a smoothly varying average refractive index with radius, with no or few discontinuities in index, and with no variation along the longitudinal axis of the preform. Apparatus and methods have therefore been developed for measuring the refractive index profile, as a means of exercising quality control in the manufacture of preforms.

P. L. Chu, in Electronics Letters, 24th Nov. 1977, Vol. 13, No. 24, pp. 736 to 738, describes a method of measuring the refractive index profile of an optical fibre preform by shining a laser beam laterally, but perpendicularly, to the preform axis and recording the exit angle $\Phi_x$ of the forward transmitted ray as a function of the distance x from the y-axis of the incident beam. A numerical integration involving those exit angles was then used to yield the refractive index profile. Apparatus for carrying out this method is disclosed by P. L. Chu and T. Whitbread in Electronics Letters, 10th May 1979, Vol. 15, No. 10, pp. 295 and 296.

GB-A-2071315 discloses a method of sensing radial variations in the refractive index of an approximately cylindrical object, such as an optical fibre preform, comprising illuminating the object over the distance to be measured with a collimated beam of light substantially normal to the axis of the object, focusing the light transmitted by the object in a focal plane parallel to a plane containing the axis of the object, modulating the beam so that a property of the light varies as a function of the distance from the optical axis in the focal plane, measuring a parameter of the focused light beam as a function of the distance of the point of measurement from the axis and deriving the radial variations in refractive index profile from the measurements of the parameter.

Many preforms (such as VAD preforms) are now commonly manufactured from a large number of thin layers of material. Whilst the refractive index of such preforms may vary substantially within each layer, these layers are so thin that the refractive index profile as a whole appears to be smoothly varying. However, it has been discovered that, because these layers are generally thinner than the beam diameter of the illuminating laser beam, diffraction takes place and that the beam exiting from the preform then consists of several distinct parts or orders.

Japanese Patent Application No. 63-95337 discloses a preform analyser comprising a fixed aperture for selecting the zeroth order beam portion, but rejecting the higher order beam portions.

It has now been found that, while such known analysers can successfully measure the refractive index profile of an optical fibre preform of relatively simple form, spurious results can be obtained when they are used with more complex preforms, such as certain VAD preforms. The present invention seeks to overcome these problems and provide a preform analyser which can be used to measure the refractive index profile, and other previously unmeasurable parameters, for a wider range of preforms than was previously possible.

As used herein, the following terms have the following meanings. A "transverse-type analyser" includes any analyser which analyses the optical properties of a preform or other such cylindrical object by illumination of the object generally transversely to its longitudinal axis. An "illuminating beam" includes any type of light, whether visible or not, and may be a broad or narrow beam, and is suitably focussed. At any location along the beam after it has exited the object the "$\Phi_x$ direction" is the direction, generally normal to the direction of the beam at that location, in which the transmitted beam would move if the beam entering the object were moved radially across the object and the object had no axial variation in refractive index. The "$\Phi_y$ direction" is the direction orthogonal to the $\Phi_x$ direction. $\Phi_x$ and $\Phi_y$ are the radial and axial angles of refraction respectively. "Portion" in connection with the transmitted beam from the object includes both an entirely non-distinct portion of that beam and also one entirely distinct individual beam (or a part thereof) out of a group of such beams emanating from the one transmitted beam as in, for example, the case of diffraction of that transmitted beam. "Discriminating" (or "selectively discriminating") includes the selection of a single beam from a surrounding signal of zero intensity or low intensity.

According to a first aspect of the present invention there is provided a transverse-type analyser, for measuring optical properties of an approximately cylindrical transparent object such as an optical fibre or optical fibre preform, comprising illuminating means for producing an illuminating beam, a detector for sensing the illuminating beam after transmission through said object, means for holding said object between the illuminating means and the detector, and filtering means for selectively limiting the output of the detector, said filtering means being adjustable such that the detector produces a signal which is representative of only a selected portion of the transmitted beam which is refracted in the $\Phi_y$ direction.

The zeroth order beam portion of the diffraction pattern emerging from an optical fibre preform contains the information that will allow computation of the radial refractive index profile. In fact, the zeroth order beam portion will generally have the same $\Phi_x$ value as the entire beam in the absence of diffraction. However, it has been discovered that some types of preform give rise to diffraction patterns in which the zeroth order is refracted in the $\Phi_y$ direction, and it is therefore an advantage of the present invention that it allows the zeroth order beam portion (and therefore the refractive index profile) to be measured for such preforms.

Moreover, it has been found that, although the average refractive index along the axis of a preform may be essentially constant, the particular manufacturing process used may cause layers to be created which do exhibit an axial variation in refractive index. An important example of such a process is the Vapour Axial Deposition manufacturing process. In this process, the optical fibre preform is grown along its longitudinal axis by means of depositing layers axially. The aim of the process is still to produce optical fibre preforms with nearly ideal circular symmetry. For such preforms, it has now been discovered that a particular feature of the diffraction pattern caused by the interaction of the beam with the layer structure is that the zeroth order beam portion is generally not deflected in the axial direction as it passes through the preform, but that the other orders do undergo an axial deflection, and that the amount of the deflection is related to the thickness of layers. In effect, the axial layer structure of such preforms results in a rotation of the diffraction pattern by an amount directly related to the axial gradient of the layer surface. The ability to adjust the filtering means so as to discriminate portions of the transmitted beam which are deflected away from the $\Phi_x$ axis thus allows analysis of the higher diffraction orders of such preforms.

Despite the axial layer structure of such VAD preforms, the average refractive index variation is almost entirely radial rather than axial, which means that the average effect is not to deviate the beam in the axial direction. Thus the zeroth order will have a $\Phi_y$ of approximately zero.

The present inventor has discovered that, to a first approximation, a VAD preform may be treated as a simple diffraction grating, so that the basic theory which relates the spacing of diffraction orders resulting from such a simple diffraction grating (see, for example, Chapter XII of "Geometrical and Physical Optics", by R. S. Longhurst, Second Edition 1967, published by Longmans) is approximately valid for VAD preforms. Thus the zeroth order is approximately equidistant from the first orders. This discovery is of use particularly when the zeroth order beam portion is not intense enough for measurement, since it enables positional information regarding this beam portion to be obtained from a knowledge of positional information regarding beam portions of other orders.

The filtering means may be mechanical, and arranged to be capable of allowing only a selected portion of the transmitted beam to reach the detector, thereby to discriminate the selected portion from the remainder of the beam. For example, the filtering means may take the form of a screen having an aperture therein, the aperture being movable in a direction having a component parallel to the $\Phi_y$ direction.

Equally, however, the filtering means may filter the output from the detector, so as to allow only selected signals to pass, thereby discriminating a selected portion of the beam. Such a logic filter may be, for example, an electronic filter.

Logic filters of this kind are useful in the analysis of many types of preform, even if they are not adjustable. The present invention therefore also provides a transverse-type analyser, for measuring optical properties of an approximately cylindrical transparent object such as an optical fibre or optical fibre preform, comprising illuminating means for producing an illuminating beam, a detector for sensing the illuminating beam after transmission through said object, means for holding said object between the illuminating means and the detector, and means for filtering the output from the detector, so as to allow only selected signals to pass, thereby discriminating a selected portion of the transmitted beam.

It will be seen that a logic filter such as an electronic filter provides filtering means analogous to a mechanical aperture, but with certain advantages. For example, if the filter is adjustable so as to allow adjustment of the portion of the transmitted beam which is discriminated, it has the advantage over its mechanical counterpart of having no parts which can vibrate and thus disturb the accuracy of measurement, and it has the further advantage of greater speed of adjustability.

In view of the numerous analogies between a logic filter and a mechanical aperture, it will be convenient hereinafter to use the term "aperture" to embrace both forms of filtering means.

A logic filter such as an electronic filter may be used in conjunction with modulation means positioned between the object and the detector for encoding the beam in the plane of the modulation means with its own positional information. The modulation may be spatial, but advantageously the beam is temporally modulated and the filtering means temporally filters the output of the detector. The modulating means may suitably be a chopper. The convenience of using the temporal modulation means is that no changes are required to the analyser to convert it to having electronic filtering means, except circuitry or software changes.

The combination of modulating means and electronic filtering of the output of the detector can be thought of as providing an aperture at the plane of the modulating means.

For simplicity, the aperture (whether mechanical or electronic) may only be movable in one direction, such as the $\Phi_x$ or $\Phi_y$ direction.

It will be appreciated that the same analyser may comprise a combination of both an electronic and a mechanical aperture. A preferred combination is a mechanical fixed or movable aperture oriented to discriminate one or more beam portions having different $\Phi_y$ values and an electronic movable aperture oriented to discriminate beam portions having different $\Phi_x$ values, since greater speed of movement is often required in the $\Phi_x$ direction and since the temporal modulation means advantageously is used in the $\Phi_x$ direction.

The aperture may be movable in either one or several directions. If it is movable in more than one direction, it may comprise a plurality of individual fixed but translatable apertures oriented in different directions, or it may be a single translatable and rotatable aperture. It is preferred that the aperture is movable in a plane substantially perpendicular to the beam incident thereon.

It will be appreciated that for many basic types of analyser, specifically those employing a narrow illuminating beam, the beam has to be traversed across the object in order for a complete refractive index profile of the object to be obtained. This may be achieved by moving either the object or the illuminating means, although, since it is often preferred to maintain the detector in a fixed disposition relative to the illuminating means, for simplicity if this is so it is conveniently the object which is movable. In either case, it is preferred for simplicity that the aperture is movable only whilst the beam is fixed relative to the object.

The aperture itself is preferably elongate and more preferably rectangular; clearly the width, rather than the length, of the aperture is then most suited to discriminating portions of the beam. As mentioned previously, it may be either mechanical or electronic; if it is mechanical, it is preferably formed from a plate having a slit therein.

The aperture is preferably of a size that just accepts the whole beam when there is no diffraction, and only a portion of the beam when diffraction occurs. Preferably, it is large enough to accept substantially all of the beam portion pertaining to one diffraction order, but small enough to reject beam portions pertaining to other diffraction orders.

Preferably, the aperture has an adjustable separation. This enables automatic alignment and configuration of the aperture to accommodate different measurement conditions. In particular, it permits the aperture to accept accurately the beam portion of relevance. Also, it permits the relative intensities of different parts of one beam portion (or diffraction order, say), or even the entire beam profile, to be measured. This can provide useful information regarding the object, as follows.

It is well-known that the characteristics of one layer of a diffraction grating determine the overall relative intensities and shapes of the diffraction orders. This fact is utilised in grating monochromators to ensure that maximum optical intensity appears in a diffraction order higher than zero; the characteristic of the grating which achieves this is termed the "blaze" angle, (see Longhurst, Chapter XII). Thus, the knowledge of the intensities and shapes of the diffraction orders of the beam emanating from a region of the object allows the deduction of the characteristics of a single layer of the refractive index being illuminated. During manufacture, this layer was created by deposition of doped silica particles from a hot gas onto the relatively cool preform surface. The precise nature of the layer is determined by many factors, including temperature, gas composition, and movement of the preform. For example, a layer of large refractive index variation may well indicate that, although initially deposited, some of the dopant material used to modify the refractive index is evaporated by subsequent excessive temperature during the deposition cycle. Thus details of a single layer are a record of the conditions at the time of deposition, and so throughout the preform the layer structure contains a record of the conditions of manufacture of that preform. This record may be used for quality control or as a means of adjusting the deposition conditions to give optimal preform characteristics. The present invention provides the means to determine details regarding this record, and is thus of use to preform manufacturers.

Preferably, the separation of the aperture is adjustable substantially in the direction of movement of the aperture. For instance, if the aperture is elongate, suitably the width rather than the length of the aperture is adjustable, although the aperture could of course be adjustable in several directions.

According to a further aspect of the invention, there is provided a transverse-type analyser, for measuring optical properties of an approximately cylindrical transparent object such as an optical fibre or optical fibre preform, comprising illuminating means for producing an illuminating beam, a detector for sensing the illuminating beam after transmission through said object, means for holding said object between the illuminating means and the detector, and filtering means for selectively limiting the output of the detector, said filtering means being adjustable whereby to discriminate a plurality of distinct portions of the beam exiting from the object.

As used in relation to this aspect of the invention, the term "distinct" connotes portions of the beam having separate intensity peaks (or troughs).

This aspect of the present invention is based on the discovery that, for preforms where diffraction occurs, the intensities and angles of deflection of the various orders are determined by the size and structure of the layers. The invention thus provides a way of analysing the intensities and angles of deflection of the various orders, in order to obtain important information regarding the structure of the preform. In accordance with the invention, this involves selecting a specified portion of the beam exiting the object, by adjusting the filtering means so as to accept one portion of the beam whilst rejecting others. Various properties of that beam portion can be measured, such as positional information or intensity.

Further, the present discovery that the theory of a simple diffraction grating is applicable to the angular separation of the different diffraction orders, not only for VAD preforms but also other preforms constructed of many thin layers which do not have an axial variation in refractive index, can be utilised in combination with this aspect of the present invention to yield positional information regarding the zeroth (or any other) order. This is particularly useful when the orders are all aligned substantially in the $\Phi_x$ direction and the zeroth order beam portion is not intense enough for measurement.

Preferably, the analyser further comprises processing means connected to the output of the detector for processing the output information regarding said plurality of distinct portions.

Suitably, the analyser, when used in combination with an object, such as a VAD preform, which diffracts the beam, comprises an aperture which is movable from a position where a beam portion pertaining to one diffraction order can be discriminated to at least one other position where a beam portion having a different diffraction order can be discriminated. It is advantageous that all the diffraction orders can be discriminated in this way, but if this is not the case, it is preferred that the one order is the zeroth order.

Preferably, the analyser further comprises means for separating portions of the beam at the plane of the aperture. Thus, if diffraction occurs, these separating means (preferably in the form of optical components such as lenses) separate the different orders of the diffraction pattern so that they occupy different spatial positions at some point within the optical system, notably approximately at the position of the aperture.

In a related aspect, the present invention provides a transverse-type analyser, for measuring optical properties of an approximately cylindrical transparent object such as an optical fibre or optical fibre preform, comprising illuminating means for producing an illuminating beam, a detector for sensing the illuminating beam after transmission through said object, means for holding said object between the illuminating means and the detector, focusing means (preferably an asymmetric lens and more preferably a cylindrical lens) mounted to receive the illuminating beam, and an aperture suitable for discriminating a portion of the beam, the focusing means being located between the object and the aperture and arranged so as to focus the beam asymmetrically in the plane of the aperture.

This aspect of the present invention thus provides a means for spreading out the different portions of a diffracted beam more in one direction than another. This enables the aperture to discriminate more clearly between the different portions so that the demands upon the precision of movement of the aperture are minimised and/or the distance of the aperture from the object or any further focusing means (if provided) can be minimised.

As used in relation to this aspect of the invention, the terms "focus" and "focusing" are used widely to connote varying degrees of focusing or separating.

Preferably, the focusing means focuses the beam less sharply in the $\Phi_y$ direction than in the $\Phi_x$ direction. Indeed, the focussing means may even eliminate all variations in $\Phi_x$ at the plane of the aperture. Especially for VAD preforms, it is advantageous to spread the diffracted beam in the $\Phi_y$ direction so as to assist discrimination of the different diffraction orders.

If, as is preferred, a cylindrical lens is provided and it has its longitudinal axis oriented substantially in the $\Phi_y$ direction, the measuring function of the analyser can be retained in the $\Phi_x$ direction whilst those portions of the beam with non-zero $\Phi_y$ are spread as widely as possible. To optimise the advantageous aspects of the invention it is preferred that the aperture, which may be fixed or movable, is either close to, or actually in the plane of, the detectors. Instead of one cylindrical lens being provided, a combination of lenses may be utilised. One particularly advantageous combination is a spherical lens train between the object and the aperture, and a cylindrical lens train between the aperture and the detector. Separating the functions of the one cylindrical lens in this way allows greater design flexibility and permits the use of a cylindrical lens of lower optical quality.

Preferably, the analyser further comprises a second focussing means located between the illuminating means and the object and arranged so as to focus the beam asymmetrically at the object. Preferably also, the second focussing means cooperates with the focussing means to focus (and spread) the beam in the same direction. More preferably, the second focussing means focusses the beam less sharply in the direction of the longitudinal axis of the object than in the direction transverse to that axis. This is especially advantageous for generating well separated and narrow diffraction orders in the $\Phi_y$ direction when the object contains an axially varying layer structure.

The detector may be of many forms, as described herein, but is preferably capable of measuring the intensity of the beam or beam portion incident thereon. This is advantageous since it has now been found that measurement of the relative intensities of different portions of the beam may be useful in the analysis of the characteristics of the object. If the detector is capable only of measuring intensity, it preferably has a sensitive area sufficiently large to detect all the relevant portions of the beam, in which case it is preferred that the aperture is movable relative to the detector. The analyser then preferably further comprises modulating means to encode the different portions of the beam according to their angular deviations (for example, $\Phi_x$). If the detector has a smaller sensitive area, it is preferably movable with the aperture, whereby all light accepted by the aperture is incident on the sensitive area.

Preferably the analyser further comprises interpolation and extrapolation means for calculating positional information concerning the beam portion pertaining to one diffraction order from positional information concerning the beam portions pertaining to other diffraction orders.

This is advantageous since, according to one of the present discoveries, for certain preforms the intensity of the zeroth order beam portion or, in fact, any order beam portion may be small or practically zero, in which case obviously its position is unmeasurable. However, it has now been discovered that in general the $\Phi_y$ versus $\Phi_x$ plot of the various diffraction orders is practically linear for small diffraction angles, so that positional information regarding the diffraction orders can be deduced from linear interpolation or extrapolation from the positions of two (or more) other orders.

Specifically, if information regarding the zeroth order beam is required, since this beam lies in general on the $\Phi_x$ axis, the above interpolation and extrapolation means may deduce the precise location of the zeroth order.

Preferably, the analyser further comprises measuring means coupled to the aperture for measuring the position of the aperture. The analyser of the present invention can thus measure the separation of the orders in a specified plane (for example, the plane in which discrimination of the illuminating beam may be thought to take place). It has now been discovered that this separation can be used to derive useful information regarding the object. More particularly, it has been discovered that the layer thickness determines the angular separation of the orders, the number of layers with respect to the entrance beam diameter determines the angular width, and the precise intensities depend upon the detailed refractive index variation within each layer. Thus, by measuring the separation of the diffraction orders emanating from a preform as a function of preform radius, information concerning the layer thickness variation within the preform can be obtained. This information, when combined with knowledge of the manufacturing process, permits the computation of the countour of the deposition surface. This is of importance in manufacturing process control, for example as discussed by K. Imoto et al. in the Journal of Lightwave Technology, Sep. 1988, Vol. 6, No. 9 pp. 1376 to 1385. The deposition layer surface contour (which is related to the term "bottom shape" in this document) is a new parameter which has never before been utilised for a preform after it has been consolidated to the glass form.

The present invention also provides a method of sensing optically properties of an approximately cylindrical object, such as an optical fibre or optical fibre preform, comprising the step of illuminating the object with an illuminating beam substantially perpendicular to the axis of the object, moving an aperture in any direction oriented away from the $\Phi_x$ direction so as to discriminate at least one beam portion exiting from the object and refracted in the $\Phi_y$ direction, and detecting said beam portion.

The present invention also provides a method of sensing optically properties of an approximately cylindrical object, such as an optical fibre or optical fibre preform, comprising the steps of illuminating the object with an illuminating beam substantially perpendicular to the axis of the object and moving an aperture in the $\Phi_x$ direction to discriminate a plurality of distinct portions of the beam exiting from the object, and detecting said distinct portions.

As used in relation to this aspect of the invention, the term "distinct" connotes portions of the beam having separate intensity peaks (or troughs).

The present invention further provides a method of sensing optically properties of an approximately cylindrical object, such as an optical fibre or optical fibre preform, which diffracts the illuminating beam into a plurality of beam portions each corresponding to its respective diffraction order, comprising the steps of illuminating the object with an illuminating beam substantially perpendicular to the axis of the object, moving an aperture so as to discriminate a beam portion exiting from the object and corresponding to a selected diffraction order, and detecting said beam portion.

If the line joining the various orders in the plane of the aperture is a straight line, the aperture may be moved in any direction relative thereto except perpendicularly to the line, although preferably the aperture is either moved in a direction substantially parallel to that line, or, for simplicity, in the $\Phi_y$ or $\Phi_x$ directions.

Suitably, the illuminating beam is narrow compared to the diameter of the object, and the method further comprises the step of moving the beam transversely relative to the object before the moving and detecting steps. If the moving and detecting steps are not repeated for a plurality of diffraction orders, then one particular order can be tracked as the beam is moved.

Preferably, where the method is for obtaining information concerning a selected diffraction order at a plurality of radial locations on the object, the object having an axial variation in refractive index, the aperture is elongate and has its longitudinal axis aligned substantially in the $\Phi_x$ direction, and in the detecting step a plurality of beam portions corresponding to the selected diffraction order are detected, by moving said beam transversely relative to the object whilst the aperture is kept substantially fixed.

Keeping the aperture substantially fixed affords a considerable reduction in the time taken to carry out a series of measurements, and is made possible by virtue of the inventor's discovery that, for objects having an axial variation in refractive index, a specified order always has only one $\Phi_y$ value, regardless of the radial location at which the illuminating beam enters the object.

It will be appreciated that the various aspects of the invention may be used in any combination, one with another.

The discoveries and theories underlying the invention, as well as specific embodiments thereof, are now described, by way of example, with reference to the accompanying drawings, in which:

FIG. 3 shows the internal structure and typical diffraction pattern of a VAD preform;

FIGS. 11a–11g show for a second alternative embodiment of aperture, the outputs from an optical interrupt detector and a solid state detector.

Figure 1A:
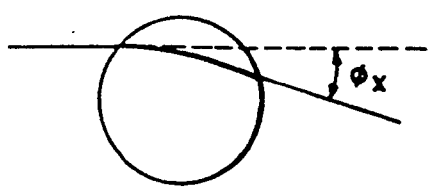
FIGS. 1a–1c illustrates the definition of $\Phi_x$ and $\Phi_y$ and shows a typical simple $\Phi_y$ versus $\Phi_x$ plot.
Figure 1B:
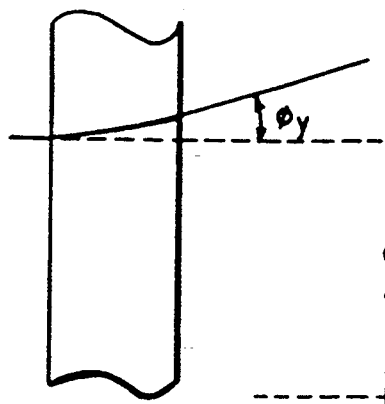
Figure 1C:
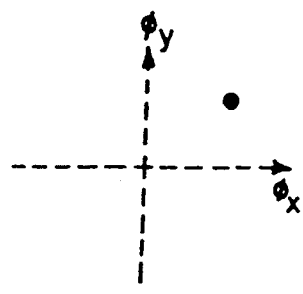
Figure 2A:
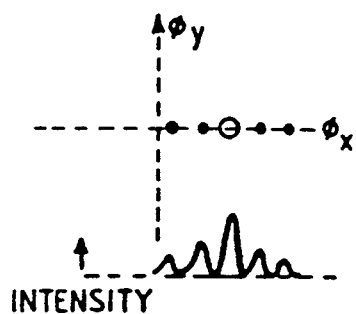
FIGS. 2a–2e are typical $\Phi_y$ versus $\Phi_x$ and intensity plots for various diffracted beams for preforms having no axial variation in refractive index.
Figure 2B:
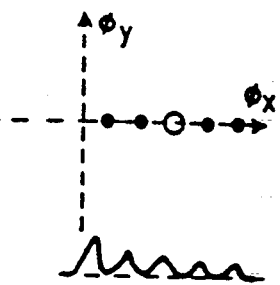
Figure 2C:
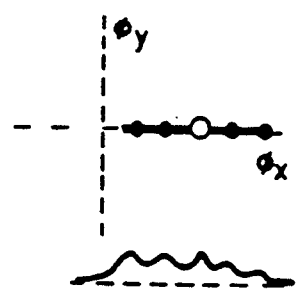
Figure 2D:
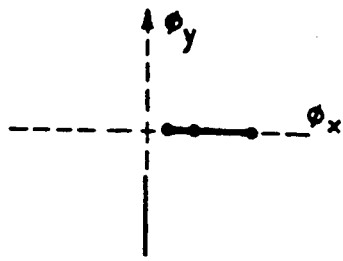
Figure 2E:
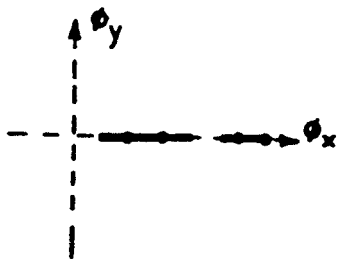

FIG. 1a illustrates $\Phi_x$, the angle of refraction of the beam in the plane normal to the longitudinal axis of the preform. FIG. 1b illustrates $\Phi_y$, the angle of refraction in the plane which includes the entrance beam and the longitudinal axis of the preform. FIG. 1c is a typical plot of $\Phi_y$ versus $\Phi_x$, for a simple preform.

In the ideal situation of cylindrical symmetry and perfectly smooth radial variation in refractive index, for any particular point of entry of the entrance beam $\Phi_x$ will be single-valued and $\Phi_y$ will be zero. Where the radial refractive index does not vary smoothly, that is, where the preform consists of layers much thinner than the beam diameter, it has been found, as described above, that the beam undergoes diffraction and divides in a number of possible different ways into a number of diffraction orders. Different examples of such diffraction orders which have been observed are shown in FIGS. 2a to 2e, in which the zeroth order is shown as an open circle in each case. Of particular interest are FIG. 2d, which demonstrates a blurring between the zeroth and first orders, and FIG. 2e, in which the zeroth order is of zero intensity.

FIG. 3 illustrates the rotation in the diffraction pattern which is observed with certain types of preform, such as VAD preforms which have an axial variation in refractive index. As discussed above, the degree of rotation of the diffraction pattern is directly related to the axial gradient of the layer surface. In this figure, t represents the layer thickness and s represents the separation of the zeroth and first order. It has been found that s is defined by the surface gradient of the relevant layer at the relevant position, and the separation of an order in the direction $\Phi_y$ from the zeroth order is directly related to t.

A particular feature of the VAD manufacturing process is that the preform is grown axially at a constant rate, and the surface on which glass soot is deposited to form the preform must retain its same shape. Otherwise, the preform would grow at different rates in different radial positions, thus making the deposition process too complex to be successful. Therefore the separation of the layers in the direction of the longitudinal axis of the preform is substantially uniform throughout the preform. It has now been discovered that the separation of the diffraction order in the $\Phi_y$ direction is independent of the radial position of the illuminating beam, so that each order lies on a locus of constant $\Phi_y$, as shown in FIG. 3.

The theory required to determine the position of a selected diffraction order from a knowledge of the positions of other diffraction orders is now described. R. S. Longhurst, in "Geometrical and Physical Optics", Second Edition 1967, published by Longmans, teaches that for a diffraction grating:

$$d*\mathrm{SIN}\,(\Delta\Phi)=p\lambda/n$$

where d is layer thickness,
$\Delta\Phi$ is the angle of deviation from the entrance beam,
p is the diffraction order and has integral value,
$\lambda$ is the wavelength of the light, and
n is the refractive index of the medium.

The value of $\Phi$ for any order may be predicted from the values of any other two diffraction orders as follows. If p is the required order and l and m are the known orders then:

$$d*\text{SIN}(\Phi_p - \Phi) = p\lambda/n$$

$$d*\text{SIN}(\Phi_l - \Phi) = l\lambda/n$$

$$d*\text{SIN}(\Phi_m - \Phi) = m\lambda/n$$

where $\Phi$ is the angle of the beam impinging upon the grating, and thus represents the average value of the grating. It is also the angle of the zeroth order. $\Phi_p$, $\Phi_l$ and $\Phi_m$ are the actual angles of deviation for the orders p, l and m respectively.

Thus, $m*\text{SIN}(\Phi_l - \Phi) = l*\text{SIN}(\Phi_m - \Phi)$, from which $\Phi$ may be derived.

This is sufficient when p=0, that is, for the zeroth order. In particular, for small deviations:

$$\Phi = (l*\Phi_m - m*\Phi_l)/(l - m)$$

However, for p not equal to zero (that is, for non-zeroth orders):

$$\Phi_p = \Phi + ASN((p/m)*\text{SIN}(\Phi_m - \Phi))$$

Equivalent expressions exist for $\Phi_x$ and $\Phi_y$, which are the projections of the deviated beam into the x-y plane. For example:

$$xd*\text{SIN}(\Phi_{xp} - \Phi_x) = p\lambda/n \qquad (v)$$

where xd is the projection of the layer thickness in the $\Phi_x$ direction, and:

$$yd*\text{SIN}(\Phi_{yp}\Phi_y) = p\lambda/n \qquad (vi)$$

where yd is the projection of the layer thickness in the $\Phi_y$ direction.

Thus, in an equivalent manner, the $\Phi_x$ value of the zeroth order may be deduced from the measurement of the $\Phi_x$ values for any other two orders.

Although only two orders are necessary to compute the above relationships to be able to estimate the position of any other order, it may well be appropriate to make an estimate from each independent pair of orders and then choose the most likely value using a procedure such as a least squares estimate so that an improved result occurs.

The ratio (yd/xd) is a constant since it is determined by the physical position and thickness of the layers in the preform. This confirms equations (v) and (vi) where the ratio yd/xd is independent of the diffraction order chosen. Thus the pairs $\Phi_{xp}$ and $\Phi_{yp}$ lie on the locus in the $\Phi_x/\Phi_y$ plane which is just the locus of all light which lies in the diffraction plane normal to the layer surface.

In certain cases, the nature of the layer structure within the preform is such that the light beam is spread sufficiently diffusely for separate diffraction orders not to be unambiguously distinguishable. On the assumption that the beam is diffused normal to the layer surface then the locus of the $\Phi_x$ and $\Phi_y$ pairs also lies on the same locus as that of the explicit diffraction orders. Therefore, the value of $\Phi_x$ for the zeroth order (when $\Phi_y$ is zero) may be obtained from the angle of the locus in the $\Phi_x$ and $\Phi_y$ plane and its intersection with the $\Phi_x$ axis simply by extrapolating the locus from measured $\Phi_x$, $\Phi_y$ pairs. These are easily obtained by positioning the moving aperture at a number of $\Phi_y$ positions, without specifically searching for identifiable diffraction orders and measuring the associated $\Phi_x$ value. When the angles of diffraction are small, the locus is a straight line which makes computation particularly simple.

The deposition layer surface contour is the shape of the intersection of a layer of deposition in the preform with the plane which contains the longitudinal axis of the preform. This shape is precisely the scaled shape of the surface of the preform during the deposition process during manufacture. The scaling arises from the fact that the preform is manufactured as layers of porous doped-silica soot, and is heated and consolidated as a transparent glass preform once deposition is finished. The process of consolidation eliminates the trapped gas and in doing so the preform undergoes diameter reduction which therefore scales the layer surface shape.

The plane of the deviation of the diffraction orders at any radial position within the preform is perpendicular to the gradient of the layers at this point. This follows from using the diffraction model assumption that at the point of measurement the preform behaves like a simple diffraction grating.

The layer gradient dy/dx of the layers in the preform is given by:

$$dy/dx = yd/xd,$$

which is evaluated by equating Equations (v) and (vi) above to give:

$$yd/xd = \text{SIN}(\Phi_{xp} - \Phi_x)/\text{SIN}(\Phi_{yp} - \Phi_y) \qquad (vii)$$

For small angle of diffraction order deviation:

$$yd/xd = (\Phi_{xp} - \Phi_x)/(\Phi_{yp} - \Phi_y) \qquad (viii)$$

Equations (v), (vi) and (vii) give the mathematical relationship between the layer gradient at a given entry point x and the corresponding measured $\Phi_x$ and $\Phi_y$ angles. Thus, measuring a minimum of two diffraction orders enables the layer surface gradient to be estimated at that radial entry point x. But the surface shape is conveniently given by y=f(x), and so using $$y = \int (dy/dx)dx$$

then $f(x) = \int (yd/xd)dx$,
where yd/xd is given by Equation (vii) or (viii).

In this way, the deposition layer surface contour, f(x), is simply obtained by numerical integration.

Figure 4:
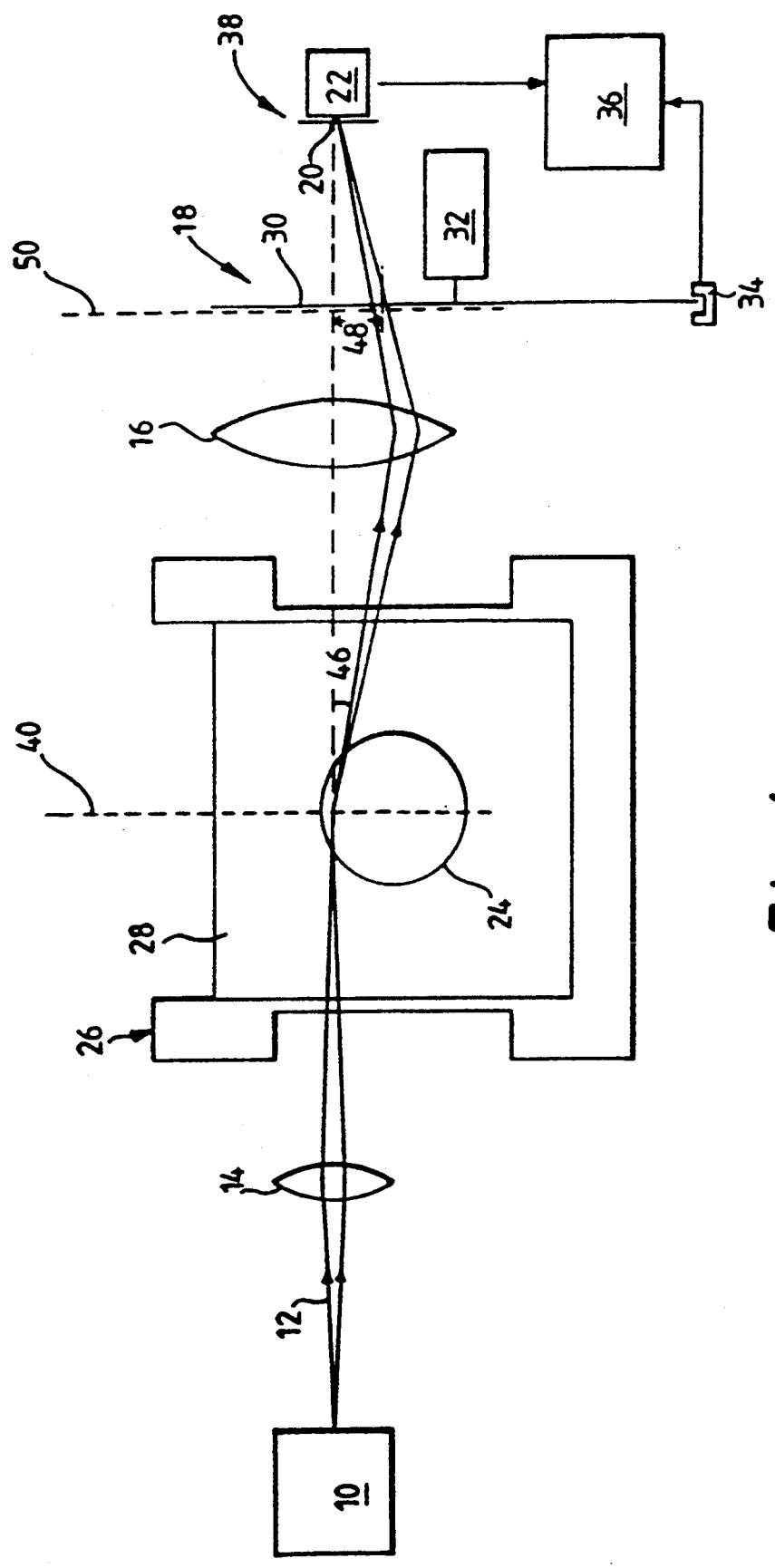
FIG. 4 is a side elevational cross-sectional view of a first embodiment of preform analyser.
Figure 5:
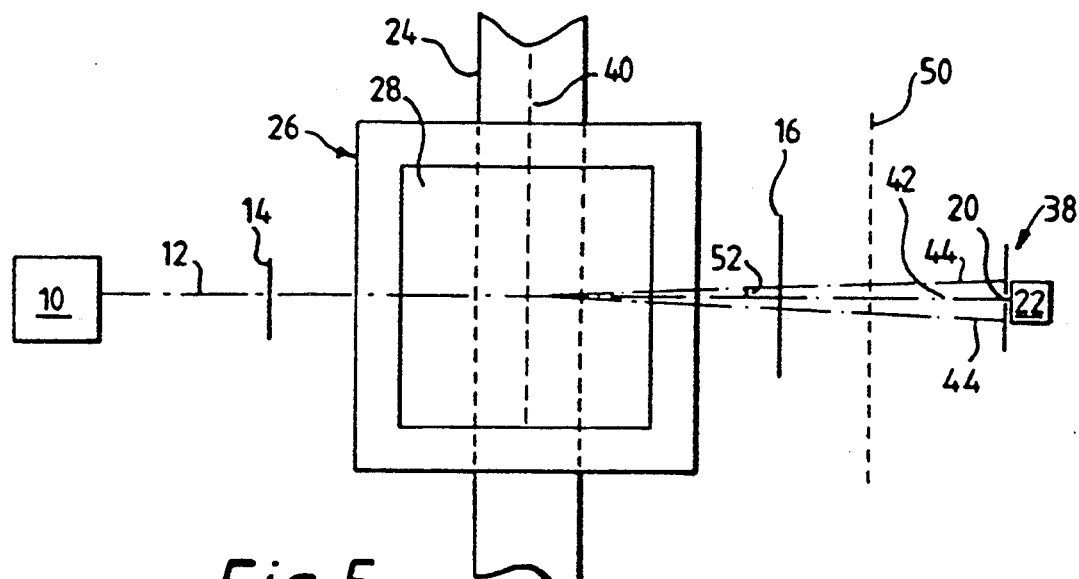
FIG. 5 is a plan view of the preform analyser of FIG. 4.

Referring to FIG. 4, a first, relatively simple, embodiment of preform analyser according to the present invention comprises a laser 10 which emits an illuminating beam 12, first and second cylindrical lenses 14, 16, a chopper 18, a slit aperture 20 and a solid state detector 22 for sensing the beam 12, all in the optical path of the beam 12. During measurement of an optical fibre preform 24, the preform 24 is placed in the optical path of the beam 12 between the first and second cylindrical lenses 14, 16 contained in a bath 26 of index matching fluid 28.

The laser 10 is a Helium Neon laser emitting light at a wavelength of 633 nm, and is movable relative to the preform 24 but with the remainder of the optical system (including lenses 14 and 16, chopper 18, aperture 20 and detector 22) in a direction roughly perpendicular to the illuminating beam 12 so as to illuminate the entire thickness of preform 24.

The chopper 18 consists of a chopper blade 30, rotatable by a motor 32, in the form of a rotating disc with alternate opaque and transparent parts, as disclosed, for instance, in United Kingdom Patent No. GB-B-2071315. An optical interrupt detector 34 is located in a fixed position relative to the chopper blade 30, and transmits a reference signal to timing apparatus 36.

The first and second cylindrical lenses 14 and 16 are mounted with their longitudinal axes aligned with the longitudinal axis of the preform 24. The asymmetry of lens 16 is used to focus the beam 12 in the plane of the aperture 20 more in the $\Phi_x$ direction than in the $\Phi_y$ direction, so that the $\Phi_x/\Phi_y$ plane is effectively squashed down to the $\Phi_y$ axis in the plane of the aperture 20 (which is the plane of the detector 22). In this way a smaller detector 22 may be used than is otherwise possible. It will be appreciated therefore that an aperture movable in the $\Phi_x$ direction could not be located at the plane of the detector 22 but would have to be located at some other plane such as focal plane 50.

Figure 6:
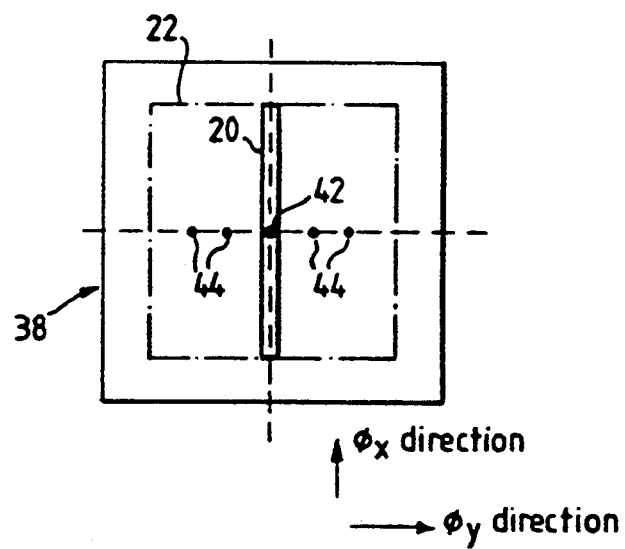
FIG. 6 is a plan view of an aperture used in the analyser of FIG. 4, together with a typical diffraction pattern at the aperture plane.

Referring now to FIG. 6, the aperture 20 is formed in an opaque plate 38, which is movable by known amounts under motor control in its own plane. The plate 38 is movable in any direction, including perpendicular to the longitudinal axis of the aperture 20. Further, the aperture 20 is itself of variable width. This is achieved by separation of plate 38 into two halves, each of which can be moved together or apart under motor control.

Alternatively, instead of both the plate 38 being movable and the aperture 20 being separable, both movement and separation of the aperture could be effected by the two halves forming the aperture 20 being movable independently in a direction perpendicular to the longitudinal axis of the aperture 20 and in the plane of the plate 38, and the plate 38 being rotatable about an axis perpendicular to its plane.

The solid state detector 22 has a sensitive area which is large compared with the area of the beam 12 at the surface thereof, as shown in FIG. 3. The detector 22 transmits information to the timing apparatus 36.

In operation, the beam 12 from the laser 10 is formed by means of the first cylindrical lens 14 on a centre plane 40 of the preform 24. Part of the beam 12 exiting the preform 24 is focused by the second cylindrical lens 16 through the aperture 20 onto the detector 22.

In the particular case exemplified in FIGS. 4 and 6, the preform 24 is a typical VAD preform, and as such has an axial variation in refractive index, and the zeroth order beam portion 42 and the higher order beam portion 44 are separated in the $\Phi_y$, but not the $\Phi_x$, direction. The longitudinal axis of the aperture 20 is orientated in the $\Phi_x$ direction and is positioned so as to accept the zeroth order beam portion 42 but reject the higher orders 44. The $\Phi_x$ deflection 46 of the zeroth order beam portion 42 is computed from the position 48 of the beam 12 in the focal plane 50 of the lens 16. This position 48 is measured by the timing apparatus 36 which determines the time difference of intersection of the chopper blade 30 with the beam 12 as determined by the detector 22 and a fixed reference signal from the interrupt detector 34. The chopper 18 thus effectively encodes the position 48 as a time difference. It will be appreciated that if only the zeroth order beam portion 42 is required to be measured, the aperture 20 could be fixed rather than movable.

The radial refractive index profile of the preform 24 is calculated from the $\Phi_x$ deflection 46 of the zeroth order beam portion 42 by the theory described, for example, in Electronics Letters Vol. 16, No. 6, pp. 219-221, 1980. The theory is in fact quite generally applicable to most types of preform.

An angular separation 52 of the diffraction orders is determined from a knowledge of the linear distance between plane 40 and the plane of the aperture 20, and by measuring the linear movement of the aperture 20 from its position for acceptance of the zeroth order beam portion 42 to acceptance of the relevant higher order beam portion 44.

Figure 7:
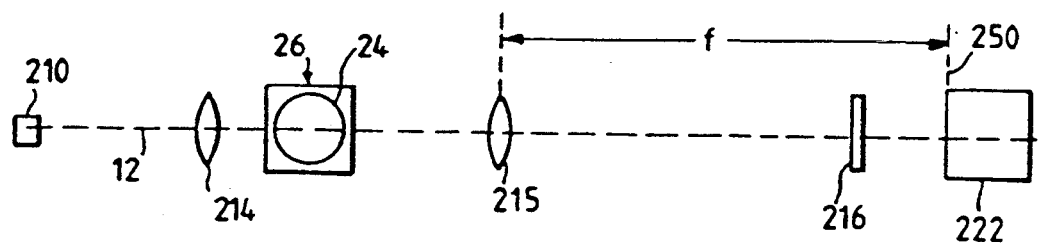
FIG. 7 is a side elevational cross-sectional view of a second embodiment of preform analyser.

The first lens 14 is not, of necessity cylindrical, although, if it is not, another cylindrical lens, fulfilling the same function as lens 216 in FIG. 7, is required to collect light onto the detector 22. In this case, the computation of the angular separation of the orders relies on the parameters of the additional lens and it is likely that discrimination in the $\Phi_y$ direction will be less successful than if lens 14 is cylindrical. Apart from these advantages, the main value of lens 14 being cylindrical is that the beam is relative broad (1 mm typically) in the axial direction of the preform but narrow (typically 25 μm) in the radial direction. The narrowness of a diffraction order is determined by the number of layers illuminated by the beam. Thus the asymmetric beam created by cylindrical lens 14 affords good optical resolution in the $\Phi_x$ direction whilst generating well separated and narrow diffraction orders in the $\Phi_y$ direction when the preform 24 contains an axially varying layer structure of refractive index. This assists in the discrimination of the orders by the aperture 20 and relaxes the constructional tolerances on the aperture 20.

The purpose of the second cylindrical lens 16 is to retain the measuring function in the $\Phi_x$ direction but to spread the higher order beam portions 44 as widely as possible so that the distance between the focal plane 50 and the aperture 20, and the demands upon precision of movement of the aperture 20, are minimised.

It will be appreciated that the present invention can be embodied in several different transverse-type preform analysers. Suitable analysers comprise two main components, namely a means of illuminating the preform substantially at right angles to its longitudinal axis, and a means of measuring the angle of refraction of light emanating from the preform. Three general classes of such analysers are now described, as the second, third and fourth embodiments of the invention, with reference to FIGS. 7 to 9 respectively. For simplicity, the position of the chopper 18 and the means for moving the preform, or the light source, so as to select different radial parts of the preform, are not shown. In the various figures, like parts are denoted by like reference numerals.

Referring to FIG. 7, in the second embodiment, a light source 210 supplies a narrow beam of light, lenses 214 and 215 may be spherical, cylindrical or omitted and lens 216 may be cylindrical or omitted. Detector 222 may be of any form which permits one or two dimensional spatial discrimination of the light falling on it, and may be at any distance from lens 215, although it is preferably in the focal plane 250 of lens 215 when present. An analyser having lenses 214, 215 spherical, lens 216 cylindrical, and the detector 222 a linear position sensor in focal plane 250 is disclosed by L. S. Watkins, Applied Optics, 1st Jul. 1979, Vol. 18, No. 13, pp. 2214 to 2222. An analyser having lenses 214, 215 spherical, lens 216 omitted and the detector 222 a television camera surface at focal plane 250 is disclosed in Japanese Patent Application No. 63-95336.

Figure 8:
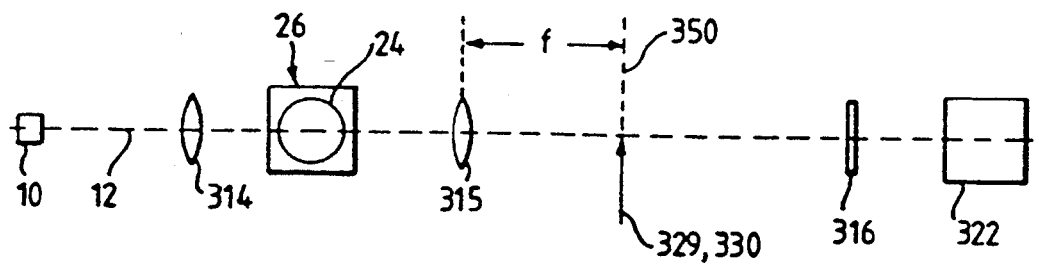
FIG. 8 is a similar view of a third embodiment of preform analyser.

In the third embodiment, shown in FIG. 8, lenses 314, 315 and 316 may again be spherical, cylindrical or omitted and lens 316 may be cylindrical or omitted. Detector 322 differs from that of the second embodiment in that it is a single light sensitive surface, incapable of spatial discrimination, of sufficient area to capture all light relevant to the measurement. The angle of refraction $\Phi_x$ of the beam 12 is measured by modulating the beam 12 either spatially or temporally.

Spatial modulation is achieved by using a knife edge 329, which may be positioned practically anywhere in the optical path between the preform 24 and the detector 322, although a preferred location is the focal plane 350 of the lens 316. The knife edge 329 is moved so as to block the beam 12 reaching the detector 322 to some extension, for example half maximum intensity. The position of this knife edge 329 in the $\Phi_x$ direction is used to compute the angle of refraction.

Temporal modulation is achieved by means of a rotating chopper 330, which is effectively analogous to a repetitively moved knife edge. The operation of the chopper 330 has been described previously.

Figure 9:
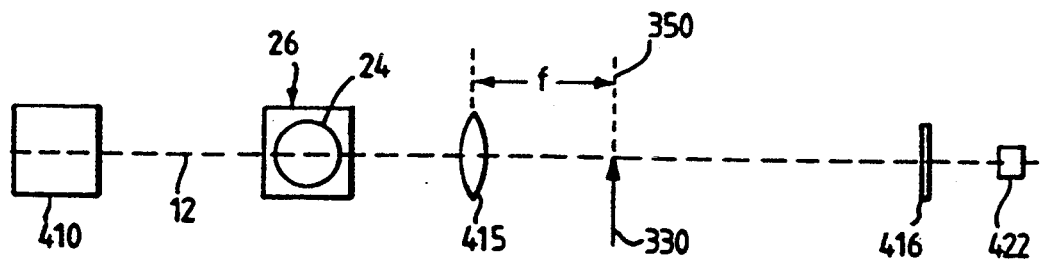
FIG. 9 is a similar view of a fourth embodiment.

The fourth embodiment shown in FIG. 9 has the distinctive feature that the light source 410 is broad beam and typically incoherent, and selection of the part of the preform 24 being measured is achieved by the imaging system of lens 415, which may be spherical or cylindrical, and detector 422, which is a single light-sensitive surface which is small at least in the $\Phi_x$ direction. Lens 416 may be either cylindrical or omitted. As was the case in the third embodiment, $\Phi_x$ is measured using temporal or spatial modulation.

The aperture 20 may be located at almost any position between the preform 24 and the detectors 222, 322 or 422 in any of the second, third or fourth embodiments. The preferred position in the second embodiment is between lens 215 and 216. The respective preferred positions in the third and fourth embodiments are at the focal planes 350, 450 of lenses 315 and 415, if the lenses are spherical, close to lenses 316 and 416 if lenses 315 and 415 are cylindrical, or, if lenses 316 and 416 are omitted, close to the detectors 322 and 422.

It will be appreciated that the third and fourth embodiments possess advantages over the second embodiment in terms of their increased potential for accurate measurement, in that they do not rely on the dimensional resolution of a two-dimensional screen but on the potentially greater accuracy of the temporal or spatial modulation means.

Figure 10:
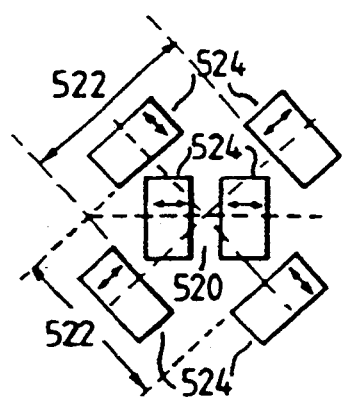
FIG. 10 is a plan view of a first alternative embodiment of aperture.

A first alternative embodiment of aperture is shown in FIG. 10. The aperture 520 effectively consists of three differently oriented independent apertures 522, each formed from two half plates 524, each of which is movable in a direction perpendicular to the longitudinal axis of its respective aperture 522, but is not rotatable. Whereas with the aperture 20 of the first embodiment shown in FIG. 3 the aperture 20 is movable in any direction (that is, is effectively rotatable to any orientation), in this first alternative embodiment the aperture 520 is effectively only movable in three fixed directions. One specific direction is selected by opening up two of the individual apertures 522 and closing down one individual aperture 522. It will be appreciated that two individual apertures orthogonal to each other could alternatively be provided.

Figure 12A:
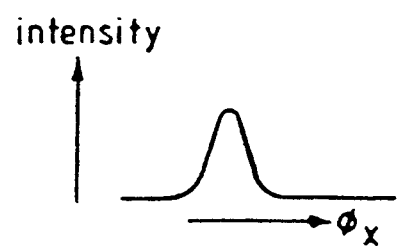
FIGS. 12a and 12b show typical intensity plots for a diffracted beam.

A second alternative embodiment of aperture is shown in FIGS. 11 and 12. The mechanical aperture of the first embodiment and first alternative embodiment processes the beam before it is detected by the detector. In this present embodiment an electronic aperture is provided, which effectively processes the beam after it has been detected by the detector. The electronic aperture essentially utilises the chopper 18, detector 22 and timing apparatus 36 of the first embodiment, but with appropriately modified circuitry in the timing apparatus 36 of that embodiment.

In outline, the chopper 18 temporally encodes the beam 12, the detector 22 turns the temporally encoded beam 12 into a signal and the timing apparatus 36 is modified so as to shut off the signal for a certain period of time, this period of time representing the width of the aperture. The aperture may thus be thought of as being in the plane of the chopper 18.

Figure 12B:
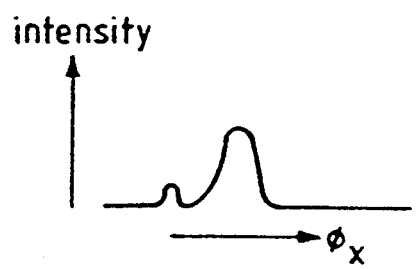

In more detail, referring to FIGS. 11, the reference signal 610 shown in FIG. 11a is generated by the interrupt detector 34 of the first embodiment. If the beam 12 incident on the chopper 18 is aligned on the $\Phi_x$ axis and has the form shown in FIG. 12a, the chopper 18 temporally encodes this beam 12 so as to be turned by the detector 22 into the signal denoted by line A in FIG. 11b. The time T is a measure of the angle of deviation of the beam 12 as described, for instance, in GB-A-2071315. However, when the beam 12 is split into distinct diffraction orders, as shown in FIG. 12b, then the signal from the detector 22 takes the form of line B of FIG. 11b, in which case time interval T no longer provides a relevant measurement of beam deviation.

The electronic moving aperture operates by switching on and off the signal denoted by line B at times analogous to the edges of a spatial aperture. This may be achieved either by circuitry or by software. Time portions of the signal are thus selected in an analogous manner to the selection of portions of the optical beam in space by the moving mechanical aperture. For instance, different parts of the signal B of FIG. 11b may be selected to give either the signal C of FIG. 11c or the signal D of FIG. 11d. It is to be noted that the form of the signals C & D is such as to permit them to be processed by precisely the same signal processing and computing means as is used for the signal A in FIG. 11b.

A circuit to implement this embodiment of aperture will now be described. Mathematically, the requirement on the aperture circuit to convert signal B of FIG. 11b to signal D of FIG. 11d is described by the following set of equations, where $V_{in}(t)$ is the signal from the detector 22 and is the voltage input to the aperture circuit, and $V_{out}(t)$ is the output voltage of the aperture circuit. Time period t1 to t2:

$$V_{out}(t) = V_{in}(t) - V_{in}(t1) \qquad (i)$$

Time period t2 to t3:

$$V_{out}(t) = V_{in}(t2) - V_{in}(t1) \qquad (ii)$$

Time period t3 to t4:

$$V_{out}(t) = V_{in}(t) - V_{in}(t3) + V_{in}(t2) - V_{in}(t1) \qquad (iii)$$

Time period t4 to t1:

$$V_{out}(t) = V_{in}(t4) - V_{in}(t3) + V_{in}(t2) - V_{in}(t1), \qquad (iv)$$

or $$V_{out}(t) = 0$$

since $$V_{in}(t1) - V_{in}(t2) = -(V_{in}(t3) - V_{in}(t4)).$$

t1 and t2 are the start and stop times of the aperture at the edge of the chopper blade 30 which is exposing the beam, and t3 and t4 are the equivalent at the complementary edge of the chopper blade 30 which is obscuring the beam.

Figure 13A:
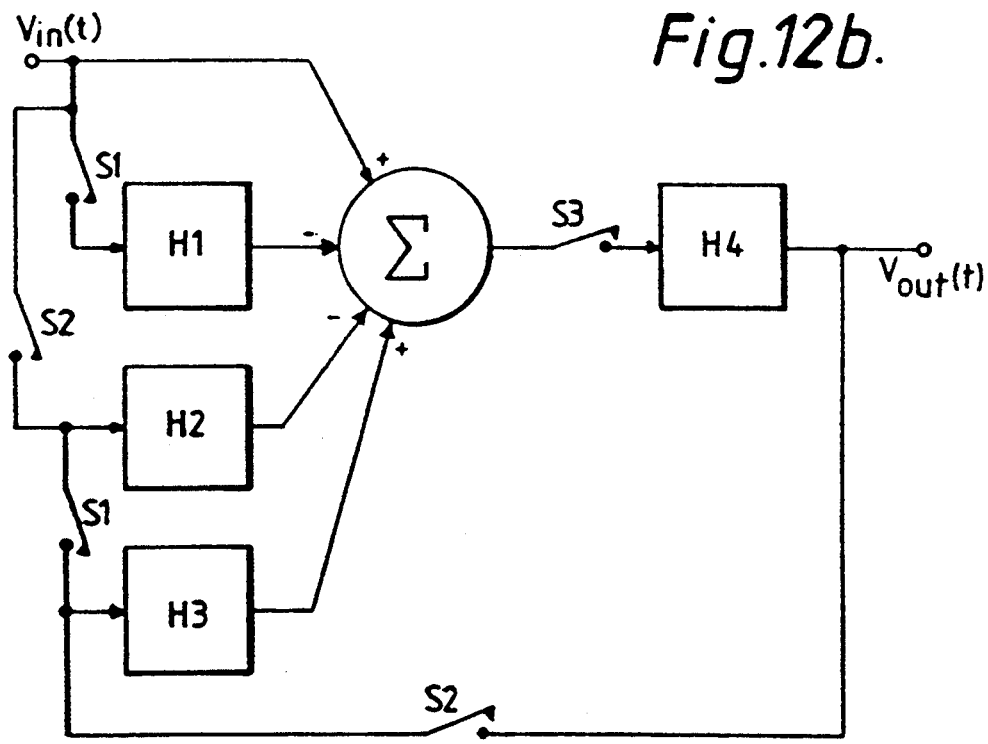
FIGS. 13a–13c are block diagrams showing the logic circuitry required in the second alternative embodiment of aperture.
Figure 13B:
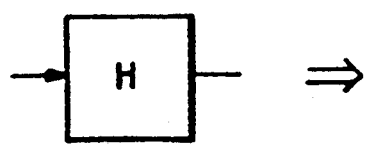
Figure 13C:
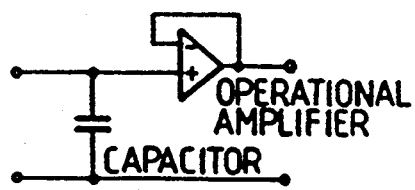

Using well-known analogue computing techniques, these equations may be implemented as shown in FIG. 13a. S1, S2 and S3 are switches which may be open or closed, the summation symbol denotes the summation of the inputs taking into account the given signs, and the memory, or hold, block is typically implemented electrically as shown in FIG. 13b.

The method of operation of the aperture circuit of FIG. 13a is now explained with reference to FIGS. 11e to 11g, where the states of switches S1, S2 and S3 are shown, each switch being closed at the higher of the two values of its respective control signal. At time t1, S3 closes, S1 opens, and S2 remains closed, with the effect that the output of block H1 is $V_{in}$ (t1), and so Equation (i) is implemented up until time t2. At time t2, when S3 opens, S1 remains open, and S2 closes, the output of H1 remains $V_{in}$(t1), the output of H3 takes value $V_{in}$(t2), and the output of H2 takes value $V_{in}$(t), and so Equation (ii) is implemented up until time t3. At time t3, when S3 re-opens, S1 remains open, and S2 closes, the output of H1 remains $V_{in}$(t1), the output of H3 remains $V_{in}$(t2), the output of H2 is $V_{in}$(t3), and so Equation (iii) is implemented up until time t4. At time t4, when S3 re-opens, S1 closes and S2 remains open, and the output becomes zero as required by Equation (iv).

Times t1 and t3 are determined as specified times after the reference signal 610 and are implemented by a programmable digital counter. The values of t1 and t3 are selected by a computer programme which controls the electronic aperture. Thus the start edge of the aperture is determined with respect to the reference signal 610. The effective width of the aperture, that is, times t2−t1 and t4−t3, is determined by a second programmable counter. The precise value of the width is selected by the computer programme controlling the aperture. The control signals selecting the states of switches S2 and S3 are derived from S3 by standard digital logic circuits such as D-edge flip-flops and NAND gates.

It will be appreciated that, although this description has been given for-the situation of two distinct beam portions which lead to signal B in FIG. 11b, the circuit operates for any shaped waveform with complementary falling and rising edges and so may be used to characterise the shape of any light beam intercepted by the chopper blade 30.

It will be understood that in order to achieve movement of the electronic aperture the times at which the signal is switched on and off will need to be varied, whilst a fixed electronic aperture could be achieved by simply maintaining those times constant. It will also be understood that, as described above, the electronic aperture is only movable in one direction, that direction being determined by the direction of movement of the chopper blade through the beam. For reasons explained elsewhere, it is normally preferred that this direction is the $\Phi_x$ direction. Usually, encoding in the $\Phi_x$ direction only is achieved by using radial edges to the chopper blade 30. However, non-radial, and non-straight edges may be used to encode in both the $\Phi_x$ and $\Phi_y$ directions as described by GB-A-2071315 at p.7 line 7, for encoding by means of the "mark-space" ratio. In this way, the electronic aperture may be used for discrimination in both the $\Phi_x$ and $\Phi_y$ directions.

It will of course be understood that the present invention has been described purely by way of example, and modifications of detail can be made within the scope of the invention.

I claim:

1. A transverse-type analyser, for measuring optical properties in an approximately cylindrical transparent object, such as an optical fibre or optical fibre preform, which diffracts light incident upon it, the analyser comprising illuminating means for producing an illuminating beam which is incident upon said object in a direction which is transverse to the longitudinal axis of said object, a detector for sensing the beam transmitted through said object, means of holding said object between the illuminating means and detector, and filtering means for selectively limiting the output of the detector, said filtering means being adjustable such that the detector produces a signal in response to, and in dependence upon, that portion of the transmitted beam which is the result of diffraction of the illuminating beam by said object in a direction parallel to the longitudinal axis thereof and corresponds to the nth diffraction order, where n is preselected and is non-zero.

2. An analyser according to claim 1 wherein the filtering means is adjustable so as to selectively filter substantially in the direction parallel to the longitudinal axis of the object.

3. A transverse-type analyser, for measuring optical properties in an approximately cylindrical transparent object, such as an optical fibre or optical fibre preform, which diffracts light incident upon it, the analyser comprising illuminating means for producing an illuminating beam which is incident upon said object in a direction which is transverse to the longitudinal axis of said object, a detector for sensing the beam transmitted through said object, means for holding said object between the illuminating means and the detector, and filtering means for selectively limiting the output of the detector, said filtering means being adjustable such that the detector produces a signal in response to, and in dependence upon, those portions of the transmitted beam which correspond respectively to preselected diffraction orders, at least one of which is a non-zeroth diffraction order resulting from diffraction of the illuminating beam by said object in a direction parallel to the longitudinal axis thereof.

4. An analyser according to claim 3 further comprising processing means connected to the output of the detector for processing the output thereof.

5. A transverse-type analyser, for measuring optical properties in an approximately cylindrical transparent object, such as an optical fibre or optical fibre preform, which diffracts light incident upon it, the analyser comprising illuminating means for producing an illuminating beam which is incident upon said object in a direction which is transverse to the longitudinal axis of said object, a detector for sensing the beam transmitted through said object, means for holding said object between the illuminating means and the detector, and adjustable means for filtering the output from the detector such that only signals produced by said detector in response to, and in dependence upon, those portions of the transmitted beam which correspond respectively to preselected diffraction orders, at lest one of which is a non-zeroth diffraction order resulting from diffraction of the illuminating beam by said object in a direction parallel to the longitudinal axis thereof, are allowed to pass.

6. An analyser according to claim 5 comprising modulation means between the object and the detector for encoding the beam in the plane of the modulation means with its own positional information for detection by the detector.

7. An analyser according to claim 6 wherein the modulation means modulates the beam temporally and the filtering means temporally filters the output of the detector.

8. A transverse-type analyser, for measuring optical properties in an approximately cylindrical transparent object, such as an optical fibre or optical fibre preform, which diffracts light incident upon it, the analyser comprising illuminating means for producing an illuminating beam which is incident upon said object in a direction which is transverse to the longitudinal axis of said object, a detector for sensing the beam transmitted through said object, means for holding said object between the illuminating means and the detector, focusing means for receiving the transmitted beam, and filtering means for selectively limiting the output of the detector, said filtering means being operable such that the detector produces a signal in response to, and in dependence upon, that portion of the transmitted beam which is the result of diffraction of the illuminating beam by said object in a direction parallel to the longitudinal axis thereof and corresponds to the nth diffraction order, where n is preselected and is non-zero, and said focusing means being located between the object and the detector and being arranged so as to focus the transmitted beam asymmetrically in a plane in which the filtering means acts to limit the output of the detector.

9. An analyser according to claim 8 wherein the focusing means focuses the beam less sharply in a direction parallel to the longitudinal axis of the object than in a direction perpendicular to a plane containing said axis and said illuminating beam.

10. An analyser according to claim 8 wherein the focusing means is a cylindrical lens having its longitudinal axis oriented substantially parallel to that of said object.

11. An analyser according to any of claim 8 further comprising a second focussing means located between the illuminating means and the object and arranged so as to focus the beam asymmetrically at the object.

12. An analyser according to claim 1, 3 5 or 8, wherein the filtering means is adjustable from a state in which a beam portion corresponding to one diffraction order can be discriminated, to at least one other state in which a beam portion corresponding to a different diffraction order can be discriminated.

13. An analyser according to claim 1, 3, 5 or 8, wherein the filtering means is selected such that it would just accept the whole beam if there were no diffraction, and only a portion of the beam when diffraction occurs.

14. An analyser according to any of claims 1, 3, 5 or 8 wherein the filtering means is adjustable so as to selectively discriminate beam portions of variable size.

15. An analyser according to any of claims 1, 3, 5 or 8 wherein the detector is capable of measuring intensity.

16. An analyser according to any of claims 1, 3 or 5 further comprising means for separating portions of the beam at a plane where the filtering means acts to discriminate said portions.

17. An analyser according to claim 12 further comprising interpolation and extrapolation means for calculating positional information relating to the beam portion corresponding to one diffraction order from positional information relating to the beam portions corresponding to other diffraction orders.

18. An analyser according to any of claims 1, 3, 5 or 8 further comprising measuring means coupled to the filtering means for measuring the position of a selectively discriminated beam portion.

19. An analyser according to claim 1, 3 or 8 wherein the filtering means is mechanical and is located between the object and the detector.

20. A method of sensing optically properties of an approximately cylindrical object, such as an optical fibre or optical fibre preform, which diffracts light incident upon it, comprising the steps of illuminating the object with an illuminating beam which is incident upon said object in a direction substantially perpendicular to the longitudinal axis of the object, moving an aperture in a selected direction which is not perpendicular to a plane containing the illuminating beam and the longitudinal axis of the object so as to discriminate that portion of the beam transmitted through said object which is the result of diffraction of the illuminating beam by said object in a direction parallel to the longitudinal axis thereof and corresponds to at least the nth diffraction order, where n is preselected and is non-zero, and detecting said beam portion.

21. A method of sensing optically properties of an approximately cylindrical object, such as an optical fibre or optical fibre preform, which diffracts light incident upon it, comprising the steps of illuminating the object with an illuminating beam which is incident upon said object in a direction substantially perpendicular to the longitudinal axis of the object, moving an aperture in a direction perpendicular to a plane containing the illuminating beam and the longitudinal axis of the object so as to discriminate those portions of the beam transmitted through the object which correspond respectively to preselected diffraction orders, at least one of which is a non-zeroth diffraction order resulting from diffraction of the illuminating beam in a direction parallel to the longitudinal axis thereof, and detecting said beam portions.

22. A method of sensing optically properties of an approximately cylindrical object, such as an optical fibre or optical fibre preform, which diffracts light incident upon it, comprising the steps of illuminating the object with an illuminating beam which is incident upon said object in a direction substantially perpendicular to the longitudinal axis of the object, moving an aperture so as to discriminate that portion of the beam transmitted through said object which is the result of diffraction of the illuminating beam by said object in a direction parallel to the longitudinal axis thereof and corresponds to at least the nth diffraction order, where n is preselected and is non-zero, and detecting said beam portion.

23. A method according to claim 22 wherein the moving and detecting steps are repeated for a plurality of selected diffraction orders.

24. A method according to claim 22 wherein said illuminating beam is narrow compared to the diameter of the object, and further comprising the step of moving the beam transversely relative to the object before the moving and detecting steps.

25. A method according to claim 22 for obtaining information concerning a selected diffraction order at a plurality of radial locations on said object, said object having an axial variation in refractive index, wherein the aperture is elongate and has its longitudinal axis aligned substantially in a direction perpendicular to a plane containing the illuminating beam and the longitudinal axis of the object, and wherein in the detecting steps a plurality of beam portions corresponding to the selected diffraction order are detected by moving said beam transversely relative to the object, whilst the aperture is kept substantially fixed.

26. A method according to claim 20 or 21, for obtaining positional information regarding a selected diffraction order exiting from the object, wherein in the moving and detecting steps a plurality of beam portions are discriminated and positional information regarding these beam portions is detected, and further comprising the step of interpolating or extrapolating from this positional information to obtain positional information regarding the selected diffraction order.

27. A method according to claim 22, for obtaining positional information regarding a beam portion corresponding to a selected diffraction order exiting from the object, wherein in the moving and detecting steps beam portions corresponding to a plurality of diffraction orders are discriminated and positional information regarding these orders is detected, and further comprising the step of interpolating or extrapolating from this positional information to obtain positional information regarding the beam portion corresponding to the selected diffraction order.

28. A method according to claim 22, suitable for determining the deposition layer surface contour of a VAD preform, the object having a structure consisting of a plurality of layers, wherein in the illuminating, moving and detecting steps positional information relating to a plurality of said beam portions is determined as a function of radial location across the object, and further comprising the steps of calculating therefrom information relating to the surface gradient of a plurality of layers as a function of said radial location, and integrating the surface gradient information to determine layer surface contour information as a function of said radial location.

29. A method according to claim 21 wherein one of the preselected diffraction orders is the zeroth order.

* * * * *